US00PP36579P2

(12) United States Plant Patent
Koot

(10) Patent No.: US PP36,579 P2
(45) Date of Patent: Apr. 1, 2025

(54) ***BUDDLEJA* PLANT NAMED 'Botex 009'**

(50) Latin Name: *Buddleja davidii*
Varietal Denomination: Botex 009

(71) Applicant: Johannes Adrianus Maria Koot, Kaatsheuvel (NL)

(72) Inventor: Johannes Adrianus Maria Koot, Kaatsheuvel (NL)

(73) Assignee: BOTANIC EXPERIENCE B.V., Kaatsheuvel (NL)

( * ) Notice: Subject to any disclaimer, the term of this patent is extended or adjusted under 35 U.S.C. 154(b) by 0 days.

(21) Appl. No.: 18/884,264

(22) Filed: Sep. 13, 2024

(30) Foreign Application Priority Data

Sep. 13, 2023 (QZ) ..... PBR 20231783

(51) Int. Cl.
*A01H 5/00* (2018.01)
*A01H 6/00* (2018.01)

(52) U.S. Cl.
USPC ..... Plt./242
CPC ..... *A01H 6/00* (2018.05)

(58) Field of Classification Search
USPC ..... Plt./227, 242
See application file for complete search history.

(56) References Cited

U.S. PATENT DOCUMENTS

PP28,177 P2 * 7/2017 Hansen ..... A01H 5/02
Plt./242

* cited by examiner

*Primary Examiner* — Karen M Redden
(74) *Attorney, Agent, or Firm* — Penny J. Aguirre

(57) ABSTRACT

A new cultivar of *Buddleja* plant named 'Botex 009' that is characterized by its very compact and dense plant habit with suitability for growing in small containers, its flowers that are fuchsia pink in color, its quick finishing; rooting within 8 weeks from a plug and quick to flower, and its neat and naturally overall rounded plant shape.

2 Drawing Sheets

Botanical classification: *Buddleja davidii.*
Variety denomination: 'Botex 009'.

BACKGROUND OF THE INVENTION

The present invention relates to a new and distinct cultivar of *Buddleja davidii* will be referred to hereafter by its cultivar name, 'Botex 009'. 'Botex 009' is a new shrub grown for use as an ornamental landscape plant and as a container plant.

The new cultivar of *Buddleja* is a selection from an ongoing breeding program conducted by the Inventor in Kaatsheuvel, The Netherlands with the goal of creating new cultivars of *Buddleja* with very neat and compact plant habits with suitability for growing in small containers combined with unique vibrant flower colors and floriferous blooming habits.

The Inventor made a cross in July of 2019 between unnamed and unpatented proprietary plants in the Inventor's breeding program. The seeds were pooled from the crosses and the exact parents are therefore unknown. The Inventor selected 'Botex 009' in August of 2022 as a single unique plant amongst the seedlings that resulted from the above cross.

Asexual propagation of the new cultivar was first accomplished by the Inventor using stem cuttings in Kaatsheuvel, The Netherlands in 2022. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Botex 009' as a unique cultivar of *Buddleja.*

1. 'Botex 009' exhibits a very compact and dense plant habit with suitability for growing in small containers.
2. 'Botex 009' exhibits flowers that are fuchsia pink in color.
3. 'Botex 009' exhibits quick finishing; rooting within 8 weeks from a plug and quick to flower.
4. 'Botex 009' exhibits a neat and naturally overall rounded plant shape.

'Botex 009' can be compared to the *Buddleja* cultivars 'Miss Molly' (U.S. Plant Pat. No. 23,425), 'Botex 005' and 'Botex 008'. 'Miss Molly' differs from 'Botex 009' in having a taller plant height, a less compact plant habit, inflorescences that are less compact and longer, and flowers that are more red in color. 'Botex 005' is similar to 'Botex 009' in having a naturally compact and floriferous plant habit. 'Botex 005' differs from 'Botex 009' in being taller in height and having flowers that are lighter pink in color. 'Botex 008' is similar to 'Botex 009' in having a very compact plant habit and a naturally rounded plant habit. 'Botex 008' differs from 'Botex 009' in having a larger plant size and flowers that are magenta purple in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Dummen Orange, Cool Plants, Floral Daily, Bill Moore & Co., Ball Seed, and Zahradnictvi-spomysl.

BRIEF DESCRIPTION OF THE DRAWINGS

The accompanying color photographs illustrate the overall appearance and distinct characteristics of the new *Buddleja*. The photographs were taken of a one-year-old plant as grown in a greenhouse in a 19-cm container in Kaatsheuvel, The Netherlands.

The photograph in FIG. 1 provides a side view of the overall plant habit of 'Botex 009' in bloom.

Figure 1:
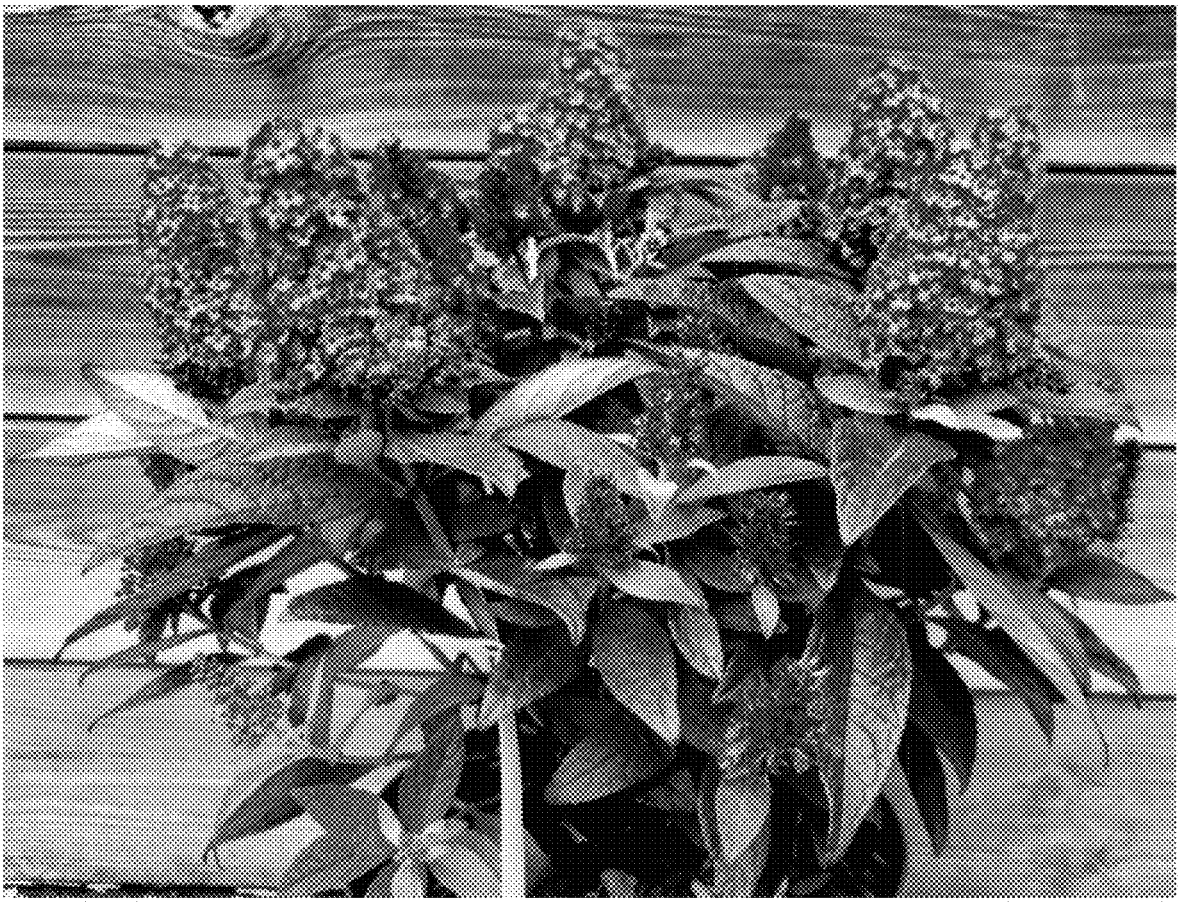
Figure 2:
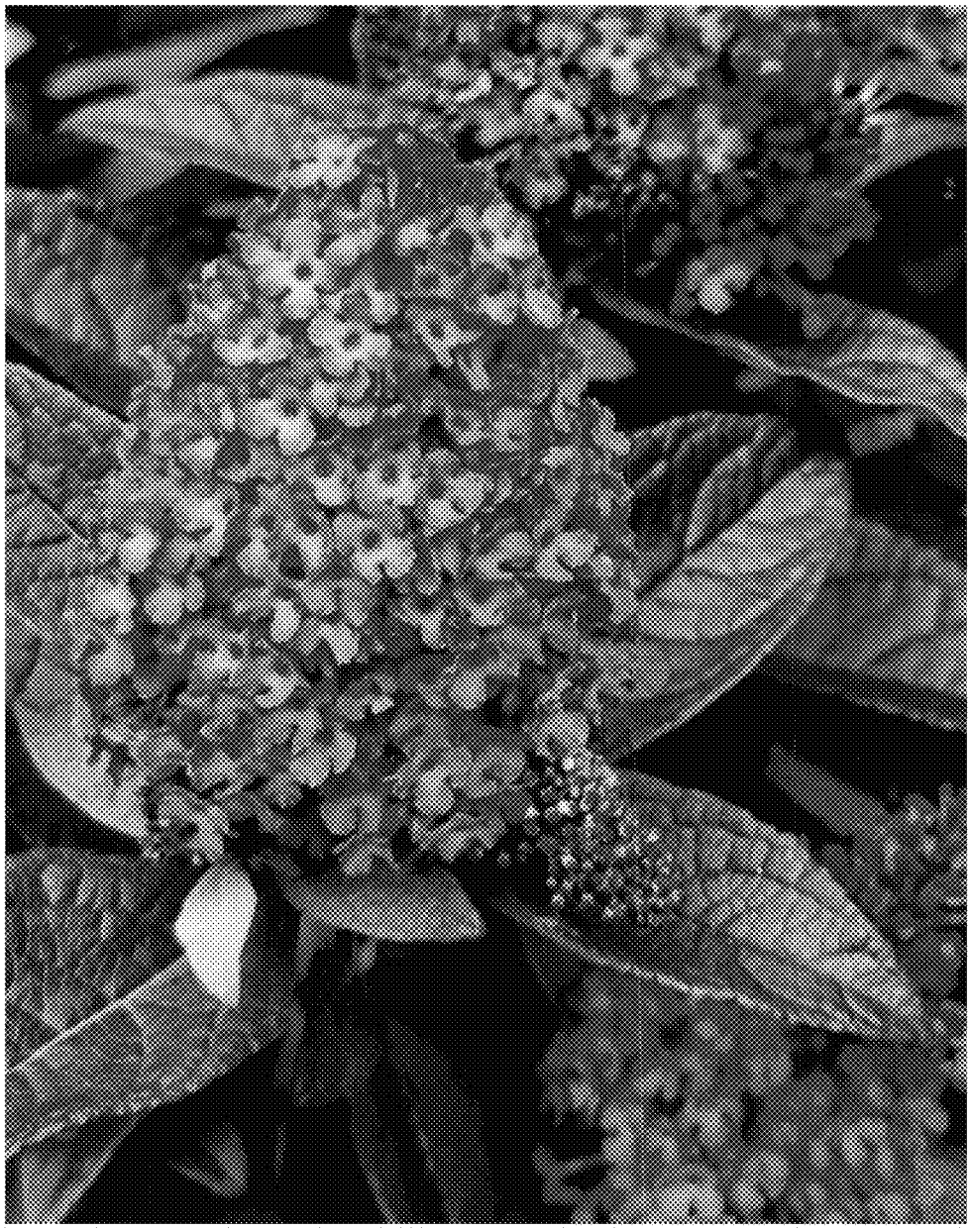

The photograph in FIG. 2 provides a close-up view of an inflorescence of 'Botex 009'.

The colors in the photographs are as close as possible with the photographic and printing technology utilized and the color values cited in the Detailed Botanical Description accurately describe the colors of the new *Buddleja*.

DETAILED BOTANICAL DESCRIPTION

The following is a detailed description of one-year-old plants as grown in a greenhouse in 19-cm containers in Kaatsheuvel, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—July to October in The Netherlands.

*Plant type*.—Deciduous perennial shrub.

*Plant habit*.—Very compact, upright and naturally rounded, dense.

*Plant size*.—An average of 29 cm in height and 36 cm in width as a one-year-old plant in a container and reaches 55 cm in height and in spread as grown in the landscape.

*Cold hardiness*.—At least in U.S.D.A. Zone 5.

*Diseases and pests*.—No susceptibility and resistance to diseases or pests has been observed.

*Propagation*.—Stem cuttings.

*Root description*.—Fibrous.

*Root development*.—4 to 5 weeks to initiate roots and 6 to 7 weeks to fully root as a young plant in a P9 container.

*Growth rate*.—Vigorous, quick finishing.

Branch description:

*Branch shape*.—Quadrangular.

*Branch color*.—Young stems; 145B, mature stems; 144A with an overlay of N187A, older woody stems; 199A.

*Branch strength*.—Strong.

*Branch size*.—Up to 18 cm in length and 5 mm in diameter.

*Branch surface*.—Pubescent.

*Branch aspect*.—Lateral stems held upright to an average angle of 30° to vertical.

*Branch internode length*.—Average of 2.3 cm.

*Branching*.—1 main branch, 6 secondary branches.

Foliage description:

*Leaf shape*.—Narrowly elliptical to lanceolate.

*Leaf division*.—Simple.

*Leaf base*.—Attenuate to cuneate.

*Leaf apex*.—Acute to slightly acuminate.

*Leaf fragrance*.—None.

*Leaf venation*.—Pinnate, color: upper surface; young 137C, mature 145B, lower surface; young 191C, mature 191B with midrib 145B.

*Leaf margins*.—Serrate.

*Leaf arrangement*.—Opposite.

*Leaf attachment*.—Petiolate.

*Leaf surface*.—Both sides are smooth, matte, and pubescent.

*Leaf size*.—Up to 7.5 cm in length and an average of 3.4 cm in width.

*Leaf quantity*.—An average of 12 per main stem.

*Leaf color*.—Young upper surface; 137C, base 137B to 137C, young lower surface; 191B to 191C, mature upper surface; NN137A, mature lower surface; 191B.

*Petioles*.—An average of 3 mm in length and 2 mm in diameter, strong, 145A in color, surface slightly pubescent.

Inflorescence description:

*Inflorescence type*.—Compound terminal and axial panicles, held upright.

*Inflorescence size*.—Up to 6.7 cm in height, up to 4.6 cm in width.

*Flower fragrance*.—Sweet, pleasant and medium strength.

*Lastingness of flowers*.—An average of 5 days, persistent.

*Flower buds*.—Oblong in shape, average of 5 mm in length and 1 mm in diameter, color; 71A.

*Flower aspect*.—Upright, slightly outward.

*Flower quantity*.—150 to 180 flowers per inflorescence, 42 inflorescences.

*Flower type*.—Single, salverform.

*Flower surface*.—All surfaces glabrous and matte.

*Flower size*.—An average of 6 mm in height, 9 mm in diameter, flower throat; 4 mm in length, 1 mm in diameter, flower tube; 3 mm in length, 1 mm in diameter.

*Peduncles*.—An average of 1.3 cm in length and 3.5 mm in diameter, held erect, 145A in color, strong, glossy and pubescent surface.

*Pedicels*.—An average of 2 mm in length and 1 mm in diameter, held at an average angle of 45°, 145B in color, strong, surface is glossy and pubescent.

*Calyx*.—Campanulate in shape, an average of 3 mm in length and 1 mm in diameter.

*Sepals*.—4, 1 whorl, rotate arrangement, fused into a campanulate shape, 3 mm in length, <1 mm in width, lanceolate in shape, acute apex, fused base, entire margin, both surfaces are matte and slightly pubescent, color; when opening and fully open upper and lower surface 145A.

*Petals*.—Average of 4, rotate, fused into salverform, 1 whorl, roughly spathulate in shape, slightly undulate margin, rounded apex, an average of 3 mm in length and 3 mm in width, upper and lower surface is glabrous and matte, color; upper and lower surface when opening; margins 71C, upper and lower surface mature; 71C and 72C, flower throat and tube inner surface; 32A and 12A at base, flower tube outer surface; 71C and 43B to 43C and 12A at base.

Reproductive organs:

*Gynoecium.*—1 pistil, 3 mm in length, style; an average of 2 mm in length, 145D in color, stigma; elongated, 1 mm in length and 145B in color, ovary is 145D in color.

*Androecium.*—Stamens; 4, filament; 4 mm in length and blend in with tube in color, anther; ovate in shape, 1 mm in length, 11D in color, pollen; low in quantity, to little to measure color.

*Fruit and seed.*—No seeds or fruit observed to date.

It is claimed:

1. A new and distinct cultivar of *Buddleja* plant named 'Botex 009' as herein illustrated and described.

* * * * *